United States Patent
Qu et al.

(10) Patent No.: US 7,243,112 B2
(45) Date of Patent: Jul. 10, 2007

(54) MULTIDIMENSIONAL BIODATA INTEGRATION AND RELATIONSHIP INFERENCE

(75) Inventors: Kunbin Qu, Foster City, CA (US); Nan Lin, Foster City, CA (US); Yanmei Lu, Foster City, CA (US); Donald G. Payan, Hillsborough, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 349 days.

(21) Appl. No.: 10/480,567

(22) PCT Filed: Jun. 14, 2002

(86) PCT No.: PCT/US02/19163

§ 371 (c)(1),
(2), (4) Date: Dec. 11, 2003

(87) PCT Pub. No.: WO02/103030

PCT Pub. Date: Dec. 27, 2002

(65) Prior Publication Data

US 2004/0162852 A1    Aug. 19, 2004

Related U.S. Application Data

(60) Provisional application No. 60/298,689, filed on Jun. 14, 2001.

(51) Int. Cl.
    *G06F 17/30* (2006.01)

(52) U.S. Cl. ............... 707/104.1; 707/102; 707/103 R; 707/3

(58) Field of Classification Search .................. 702/19, 702/20; 707/10, 104, 1, 100, 102, 200, 104.1
See application file for complete search history.

(56) References Cited

U.S. PATENT DOCUMENTS

| | | | |
|---|---|---|---|
| 5,966,712 A * | 10/1999 | Sabatini et al. | 707/104.1 |
| 6,308,170 B1 * | 10/2001 | Balaban | 707/3 |
| 6,470,277 B1 * | 10/2002 | Chin et al. | 702/19 |
| 6,553,317 B1 * | 4/2003 | Lincoln et al. | 702/20 |
| 6,675,166 B2 * | 1/2004 | Bova | 707/10 |
| 6,813,615 B1 * | 11/2004 | Colasanti et al. | 706/46 |
| 6,941,317 B1 * | 9/2005 | Chamberlin et al. | 707/102 |
| 6,950,753 B1 * | 9/2005 | Rzhetsky et al. | 702/19 |
| 2002/0052692 A1 * | 5/2002 | Fahy | 702/19 |

* cited by examiner

*Primary Examiner*—Tim Vo
*Assistant Examiner*—Dangelino Gortayo
(74) *Attorney, Agent, or Firm*—Townsend and Townsend and Crew LLP

(57) ABSTRACT

This invention provides an advanced platform for the analysis of biological data that emphasizes pathway mapping and relationship inference based upon data acquired from multiple diverse sources. The platform employs a bioinformatic system that integrates data from the diverse sources, connecting related genes and proteins and inferring biological functions in the context of global cellular processes.

18 Claims, 6 Drawing Sheets

US 7,243,112 B2

MULTIDIMENSIONAL BIODATA INTEGRATION AND RELATIONSHIP INFERENCE

CROSS REFERENCE TO RELATED APPLICATIONS

The present application claims priority under 35 U.S.C. 119(e) from U.S. Ser. No. 60/298,689, filed Jun. 14, 2001, the disclosure of which is incorporated by reference herein.

BACKGROUND OF THE INVENTION

This invention relates to systems for the collection and manipulation of biodata from diverse sources and the processing of such biodata to identify potential therapeutic targets.

The human genome project, with its goal of complete genome sequencing, has examined three gigabytes of human genomic DNA and predicts that approximately 30,000 genes are resident in the human genome. However, identification and sequencing of a gene are but the first steps in its characterization. The challenge is to determine the function of the gene as well as its relationship to other genes. With this information, directed experimentation to identify genes that are likely targets for therapeutic intervention becomes feasible and, ultimately, the drug discovery timeline will be shortened.

Genes contain genetic information that is transcribed into messenger RNA and then translated into protein. Proteins play a critical role in cellular processes. Functional proteomics seeks to identify a protein's function and related pathway roles through large-scale, high-throughput experiments. Protein functional analysis systematically determines protein-protein interactions. Protein interactions mediate cellular signaling cascades that are not typically linear, but are more likely represented by a complex branched network. When unknown proteins interact with previously characterized proteins, information about their function and role in the same or related cellular process may be obtained.

Most commercially available bioinformatics systems perform functional analysis using a single information source such as a traditional relational database optimized for transactional database processing. Such systems do not integrate collections of data from various sources. Conversely, an intelligent system that integrates data derived from multiple sources would allow for the integration of data from various operational databases and, thus, enhance research efforts which focus on specific therapeutic targets.

SUMMARY OF THE INVENTION

This invention provides an advanced platform for the analysis of biological data that relies upon pathway mapping and relationship inferences drawn from data acquired from multiple diverse sources. The platform employs a bioinformatic system that integrates data from the diverse sources, connecting related genes and proteins and inferring biological functions in the context of global cellular processes.

The invention may be conceptually understood as having four primary components: data collection, data integration, data analysis/relationship inference and inference presentation.

DETAILED DESCRIPTION OF THE INVENTION

Figure 7:
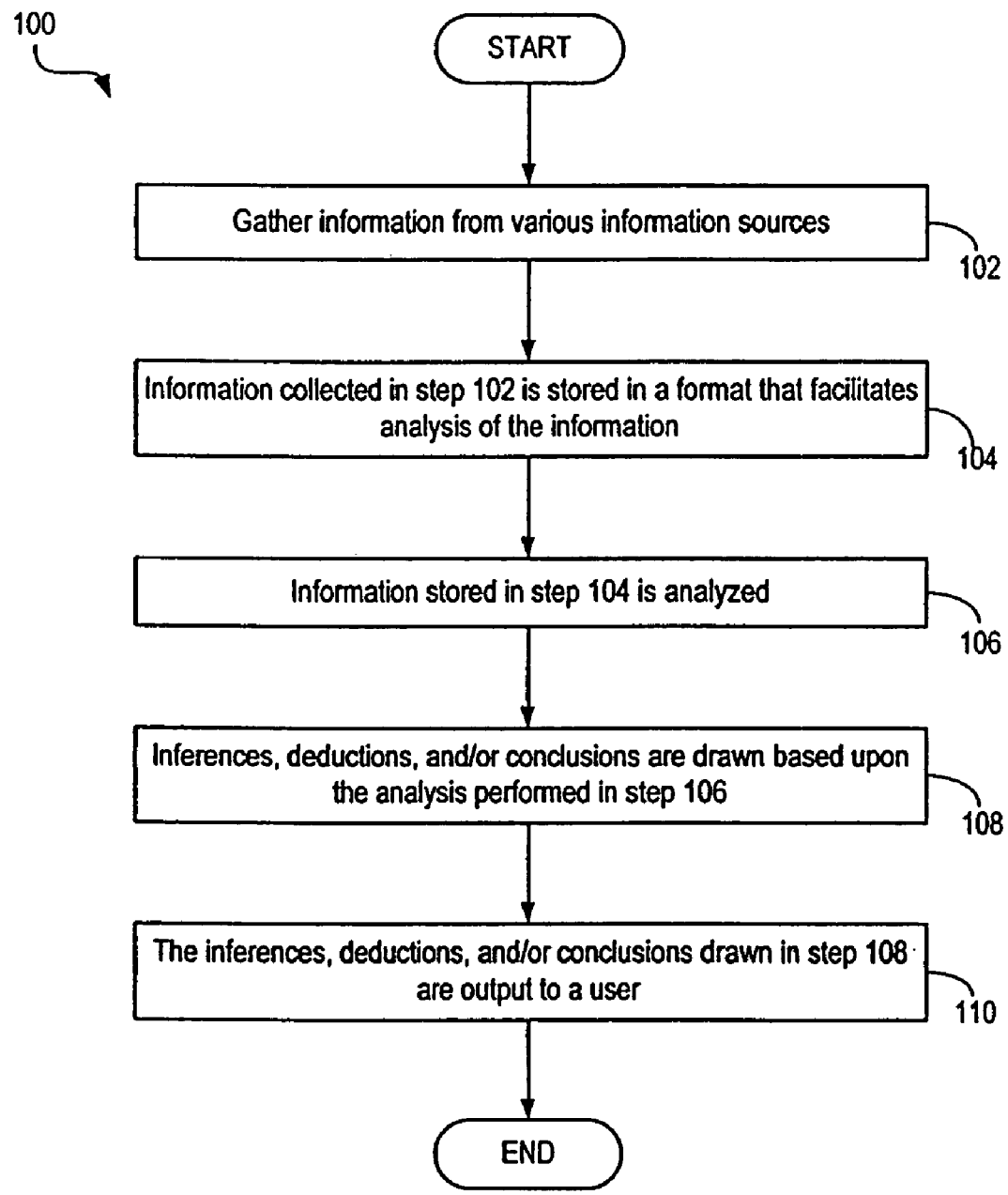
FIG. 7. Flowchart outlining the system of this invention.

Embodiments of the present invention provide techniques for identifying potential therapeutic targets. In order to identify potential therapeutic targets, an embodiment of the present invention determines characteristics of genes and proteins based upon information available from various public and private information sources. FIG. 7 is a simplified high-level flowchart 100 depicting a method of determining characteristics of genes and/or proteins based upon information available from various public and private information sources according to an embodiment of the present invention. The method may be performed by a data processing system that may comprise a memory subsystem and one or more processors. For example, the processing depicted in flowchart 100 may be performed by software modules that are stored by the memory subsystem of the data processing system and are executed by one or more processors of the data processing system. The processing may also be performed by hardware modules coupled to the data processing system, or by a combination of software modules and hardware modules. It should be understood that flowchart 100 is merely illustrative of an embodiment incorporating the present invention and does not limit the scope of the invention as recited in the claims. One of ordinary skill in the art would recognize variations, modifications, and alternatives.

As depicted in flowchart 100, information from various information sources is gathered (step 102). As described below in further detail, the information sources may include public and private information sources (e.g., publicly accessible gene databases such as GenBank, databases storing micro-array information such as the Stanford Micro-array Depository, databases that store published information such as Medline, private information sources, experiments, and the like). The information may be collected manually or in an automated manner.

The information collected in step 102 is then stored in a format that facilitates analysis of the information (step 104). As described below in further detail, the information may be stored in one or more databases that are integrated using a data warehouse-based infrastructure. According to an embodiment of the present invention, the information is also stored or represented in the form of characteristic matrices. Each characteristic matrix may store and represent information for a particular dimension of data. For example, a first characteristic matrix may store information related to functional assays, a second characteristic matrix may store information related to protein-protein interactions, a third characteristic matrix may store information related to ontology mappings, a fourth characteristic matrix may store information related to fold recognition, and on. Further information on the different characteristic matrices that may be used is described below.

The information stored in step 104 is then analyzed (step 106). Various different analysis techniques may be used. For example, according to an embodiment of the present invention, multivariate analysis techniques including clustering analysis techniques are used to analyze the information stored in step 104. According to an embodiment of the present invention, the information that is stored in databases and information that is represented by the characteristic matrices is analyzed. The characteristic matrices facilitate multidimensional analysis of the data.

Inferences, deductions, and/or conclusions are then drawn based upon the results of the analysis performed in step 106 (step 108). For example, according to an embodiment of the present invention, clustering analysis yields clusters of genes and proteins that are co-related together. Inferences can then be drawn from the clusters formed as a result of the clustering analysis. For example, genes and proteins with similar profiles based upon various biological experiments/observations that are clustered together are more likely to have similar cellular functions and be involved in the same biological pathways. As a result, characteristics of novel (or previously unknown) genes and functions of novel proteins can be inferred based upon characteristics and functions of the known genes or proteins in the same cluster. In this manner, various inferences, deductions, and conclusions can be drawn from the results of the analysis performed in step 106.

The inferences, deductions, and/or conclusions drawn in step 108 may then be output to a user (step 110). Various different techniques may be used to output the results to the user. For example, according to an embodiment of the present invention, the information may be output to the user in response to a query received from the user. Various different user interfaces may be used to output the information to the user.

The processing performed in each step of flowchart 100 is described below in further detail.

The four primary components of the multidimensional biodata integration and relationship inference platform are described in detail below.

a) Definitions

The following definitions are set forth to illustrate and define the meaning and scope of the various terms used to describe the invention.

The term "therapeutic target" means any environment or molecule (often a gene or a protein) that is instrumental to a disease process, though not necessarily directly involved, with the intention of finding a way to regulate that environment's or molecule's activity for therapeutic purposes.

By the term "biodata" is meant, for the purpose of the specification and claims, any biological data compiled in one or more database(s) and/or data warehouse including, but not limited to, biological data related to molecular pathways, cellular processes, protein-protein interaction, protein structure, genetics, molecular biology, expression arrays, functional assays, and genomes.

The term "data warehouse" refers to a repository where data from multiple databases is brought together for more complex analysis. It is also a physical repository where relational data are specially organized to provide enterprise-wide, cleaned data in a standardized format.

The term "data mart" means a subset of a data warehouse where data relevant to a particular query is stored.

The term "archival biological data" means biological data that has been archived or compiled in one or more database(s) and/or data warehouse(s) and can be accessed by a user. Examples of archival biological data are domain analyses, ontology vocabulary mapping, fold recognition, gene sequences, expressed sequence tags (ESTs), single polynucleotide polymorphisms (SNIPs), biochemical functions, physiological roles and structure/function relationships.

A "multidimensional database" as used herein, is a database in which data is organized and summarize in multiple dimensions for easier comprehension. By performing queries, users can create customized slices of data by combining various fields or dimensions.

The term "compound library" refers to a large collection of compounds with different chemical properties or shapes, generated either by combinatorial chemistry or some other process or by collecting samples with interesting biological properties. This compound library can be screened for drug targets. For example, a lead compound is a potential drug candidate emerging from a screening process of a large library of compounds.

"High-throughput screening (HTS)" refers to rapid in vitro screening of large numbers of compound libraries (generally tens to thousands of compounds), using robotic screening assays.

A "protein array" or "protein microarray" refers to a multi-spot, metallic or polymeric device with surface chemistries used for affinity capture of proteins from complex biological samples. A "protein array analysis" refers to the use of a protein array in order to evaluate potential polypeptide(s) of interest. For example, using a protein microarray made up of several hundred antibodies it is possible to monitor alterations of protein levels in specific cells treated with various agents.

A "nucleic acid array" or "DNA microarray" as used herein means a device (e.g., glass slide) for studying how large numbers of nucleic acids (e.g., cDNA, genomic DNA, RNA, mRNA, SiRNA, etc.) interact with each other and how a cell controls vast numbers of nucleic acids simultaneously. Tiny droplets containing nucleic acids are applied to slides and fluorescently labeled probes are allowed to bind to the complementary nucleic acid strands on the slides. The slides are scanned and the brightness of each fluorescent dot is measured. The brightness of the dot reveals the presence and quantity of a specific nucleic acid. A "nucleic acid array analysis" employs such arrays for the analysis of nucleic acid(s) of interest.

The term "functional gene screening" refers to the use of a biochemical assays in order to screen for a specific protein, which indicates that a specific gene is not merely present but active.

The term "expressed sequence tag (EST)" referst to a nucleic acid sequence made from cDNA which comprises a small part of a gene. An EST can be used to detect the gene by hybridizing the EST with part of the gene. The EST can be radioactively labeled in order to locate it in a larger segment of DNA A "single nucleotide polymorphism (SNP)" refers to changes in a single base pair of a particular gene happening simultaneously in a population.

The term "structure/function relationship" refers to the the relationship between the structure and organization of the gene and the function of the gene as it directs growth, development, physiological activities, and other life processes of the organism. It also refers to the structure and organization of the protein and function of the protein as cellular building block and/or participant in cellular processes and pathways.

The term "cleaned" means, for the purpose of the specification and claims, the process of mating data that is being imported into a data warehouse more accurate by removing mistakes and inconsistencies.

The term "time variant data" refers to data whose accuracy is relevant to any one moment in time. Thus, the term "time variant database" refers to a database that contains, but is not limited to, such time variant data.

"Cluster analysis", as used herein, refers to clustering, or grouping, of large data sets (e.g., biological data sets) on the basis of similarity criteria for appropriately scaled variables that represent the data of interest. Similarity criteria (distance based, associative, correlative, probabilistic) among the several clusters facilitate the recognition of patterns and reveal otherwise hidden structures.

An "supervised analysis" refers to a data analysis technique whereby a model, is built without a well defined goal or prediction field. The systems are used for exploration and general data organization. An "unsupervised clustering analysis" is an example of an unsupervised analysis.

The term "algorithm" means a procedure used to solve a mathematical or computational problem or to address a data processing issue. In the latter sense, an algorithm is a set of step-by-step commands or instructions designed to reach a particular goal or a step-by-step search, where improvement is made in every step until the best solution is found.

A "neural net" or "artificial neural network" refers to computer technology that operates like a human brain, such that computers possess simultaneous memory storage and work with ambiguous information.

A "relational database" refers to a database in which data is stored in multiple tables. These tables then "relate" to one another to make up the entire database. Queries can be run to "join" these related tables together. An "operational database" comprises system-specific reference data and event data belonging to a transaction-update system. It may also contain system control data such as indicators, flags, and counters. The operational database is the source of data for the data warehouse. The data continually changes as updates are made, and reflect the current value of the last transaction.

b) Data Collection

Data may be obtained from both experimental and archival sources. The data sources are diverse and constitute the basic input for the system. Representative data may be obtained, inter alia, from gene functional assays, protein-protein interaction studies (e.g. yeast two-hybrid screening, proteomic chip or chromatographic analyses), ontology vocabulary mapping, fold recognition, nucleic acid array expression data, gene domain analysis, and proprietary, published or otherwise publicly accessible archived gene and protein sequences, EST's, structure-function relationships, and related chemical, clinical and physical data. In a given embodiment, any number of data sources may be called upon to invoke the platform.

Functional assays. Cell cycle functional screening assays may be used to identify small fragments of genes or peptides that cause arrest at different cell cycle phases. Information associated with each assay includes experimental protocols, reagents, and raw data such as electrophoresis gel images.

Protein-protein interactions. To further characterize proteins demonstrating a desired functional assay phenotype, proteins interacting with each other may be identified through a variety of techniques, including, but not limited to yeast two-hybrid (YTH) screening and proteomic chip and chromatographic analyses.

The yeast-based two-hybrid (YTH system is a common method for large-scale experimental detection of protein-protein interactions. In YTH systems, the protein of interest (the bait) is fused to a fragment of a known DNA-binding protein such as GAL4, anchoring the bait to a calorimetric reporter gene. Potential interacting proteins (screened members expressed from a cDNA library) are then attached to a cognate transcriptional activating protein that can activate the reporter gene, producing an easily monitored color change in yeast cells. This color change results from the direct physical interaction between the proteins.

Mapping protein interactions through protein chip patterns is an alternative high-throughput methodology. In addition, 2D polyacrylamide gel electrophoresis (2D GEL) coupled with mass spectroscopy now provides proteomic fingerprints, digestion patterns of protein complexes in different cellular states.

LIMS (Laboratory Information Management Systems) is used to track large scale cloning process, sequencing and down stream data generated from different functional assays, yeast-two-hybrid screening, and proteomics experiment. Functional screens include, but are not limited to cell cycle regulation, angiogenesis, T cell activation, B cell activation, IgE class switch, etc.

For example, the goal of cell cycle functional assay is to identify genes that cause arrest at different cell cycle phases. The identified genes are then evaluated as targets for therapeutic intervention to slow tumor growth or tumor genesis. The process may be is described as follows. Cell tracker dye is applied to tumor cells that host different cDNA fragments. After several days growth, the slow replication cells are sorted out using FACS (fluorescence-activated cell sorter). The cDNA that confers this phenotype is then extracted using RT-PCR (reverse transcriptase-polymerase chain reaction). Information associated with the whole process includes experimental protocols, reagents, gene sequences, and raw data (such as histograms or dot plots generated by FACS). Raw data results from each functional assay are then transferred to data warehouse for storage.

LIMS is a task-based workflow system implemented in JAVA technology with a generic schema and open architecture. It supports various workflow patterns fork, option, loop, merge, two types of nodes (entity node, bridge node) and exit/entry conditions. Tasks are assigned based on roles or inherited from the parent tasks. A message system is used to send notices to users for pipeline modification. Security management, transaction management and resource management are also implemented in the system. The scheduler can schedule certain tasks based on one time execution or repeat execution. XML technology is used generally for the workflow descriptor and object distribution. The workflow deployment tool deploys the specific pipeline based on the descriptor. The front end of this system is browser based.

Data from public sources are gathered automatically by web crawler (written in PERL script language) or periodically dispatched UNIX processes. Various parsers are developed to extract the information we need for downstream data warehouse storage. These data sources include: ontology classification, co-regulation value based on expression array, public sequences (EST, protein and nucleotide), and individual genomes from various species as described in the following.

We use ncftp which has been scheduled by Unix cron job running every week to fetch the EST, proteins and nucleotides from NCBI at ftp://ftp.ncbi.nih.gov/blast/db. The raw data is stored on server disk. A LWP based Perl script takes three URLs (http://www.tigr.org, http://genome.ucsc.edu, http://www.fruitfly.org/) as its input and the output is parsed and stored as a text file. The following data sources are generated based on computation applied to the original data sources from the above: domain analysis, fold recognition, and protein links based on multiple genomes.

Published literature may also be used either by manually extracting information or using natural language processing (NLP) for incorporation into database.

Ontology vocabulary mapping. An ontology provides a formal written description of a specific set of concepts and their relationships in a particular domain (P. D. Karp, An Ontology for Biological Function Based on Molecular Interactions, *Bioinformatics*, vol. 16, 2000, pp. 269-285). One ontology is based upon Stanford University's Gene Ontology (GO) Consortium (www.geneontology.org). The LWP based Perl script uses HTTP GET to fetch the three ontology files (component.ontology, process.ontology, function.ontology) from the ftp site (ftp://ftp.geneontology.org/pub/go/ontology/). The files are stored on the server disk and are parsed by matrix generation program.

GO has three categories: molecular function, biological process, and cellular component. A gene product has one or more molecular functions and participates in one or more biological processes. The gene product might be a cellular component or it might be associated with one or more such components. Each element's ontology is represented on an acyclic directed graph. The nodes at the upper branches have more general characteristics, while end nodes have relatively specific attributes, including inheritance of parental, characteristics.

Fold recognition. Although there are several hundred thousand proteins in the nonredundant protein database at the US National Center for Biotechnology Information (NCBI), it is estimated that there are only about 5,000 unique native 3D structures or folds. Most frequently occurring folds were determined experimentally. PROSPECT, a threading package developed at Oak Ridge National Lab was used to predict novel gene folds (Y. Xu and D. Xu, Protein Threading Using Prospect: Design and Evaluation, *Proteins*, vol. 40, 2000, pp. 343-354). Threading searches use structure templates to find a query's best fit. PROSPECT has three components:

Libraries of representative 3D protein structures for use as templates, including protein chain (2,177 templates defined by the families of structurally similar proteins [FSSP] nonredundant set) and compact domains (771 domains defined by the distance-matrix-alignment [DALI] nonredundant domain library).

A knowledge-based energy function describing the fitness between the query sequence and potential templates.

A "divide-and-conquer" threading algorithm that searches for the lowest energy match among the possible alignments of a given query-template pair. The algorithm first aligns elements of the query sequence and the template, and then merges the partial results to form an optimal global alignment.

A neural network derives a criterion to estimate the predicted structure's confidence level. Typically, the criterion selects about five statistically significant hits for a query protein.

Coregulation from array expression. Nucleic acid arrays hybridize labeled RNA or DNA in solution to nucleic acid molecules attached at specific locations on high-density array surfaces. Hybridization of a sample to an array is a highly parallel search allowing complex mixtures of RNA and DNA to be interrogated in a high throughput and quantitative fashion. DNA arrays can be used for many different purposes, but predominantly they measure levels of gene expression (messenger RNA abundance) for tens of thousands of genes simultaneously (D. J. Lockhart and E A Winzeler, Genomics, Gene Expression and DNA Arrays, *Nature*, vol. 405, 2000, pp. 827-836). Chips with hundreds or thousands of oligonucleotide sequences representing partial gene sequences may be constructed. Hybridizing mRNA derived from different samples, for example, cancerous versus normal tissue, provides information about gene expression under different cellular conditions. Gene function may be inferred by correlating differential mRNA expression patterns.

If a gene has no previous functional assignments, one can give it a tentative assignment or a role in a biological process based on the known functions of genes in the same expression cluster (the "guilt-by-association" concept). This is possible because genes with similar expression behavior (for example, parallel increases and decreases under similar circumstances) tend to be related functionally.

Collaboratively, the National Cancer Institute (NCI) and Stanford University have tested the expression of 8,000 unique genes in 60 cell lines used in NCI's anticancer drug screening. The Stanford microarray depository website:

(http://genome-www5.stanford.edu/cgi-bin/SMD/listMicroArrayData.pl?tableName=publication&5306)

may be used as a data source. The program is implemented by PERL LWP as a Unix terminal command-based script that has been scheduled to run every month for data update. The input of the program is the Standford microarray database URL and output is the parsed ASCII-text based flat file. The program uses the GET method from the HTTP protocol to fetch the HTML-format data from the above web site, then parses the data into an ASCII-text based flat file and uses the hard disk as its secondary persistent data storage.

Domain analysis. Gene domain analysis is based on a hidden Markov models search (hmmsearch, HMMER 2.0 suite) against the Pfam model set of 2,773 domains downloaded from http://pfam.wustl.edu with an E-value cutoff of 0.0005. A multiple-thread Perl program is implemented for the domain analysis. It takes a FASTA format protein file as the input and invokes a system call to trigger the Pfam search for each protein sequence. It then parses the raw output to a hash data structure which stores domain name, e-value, alignment position/gap for each protein. The hash data structure is persistent by the Unix file system.

Protein links based on multiple genomes. HTS allows an increasing number of genomes to be sequenced. Given the assumption that genes present in the genomes of multiple species share similar evolutionary histories (phylogeny) and might therefore share similar functions, Eisenberg and colleagues proposed to infer potential protein-protein links from genes with similar phylogenetic profiles (D. Eisenberg et al., Protein Function is the Post-Genomic Era, *Nature*, vol. 405, 2000, pp. 823-826). Approximately 50 completed genomes from the Institute for Genome Research and the Sanger Center were used to generate phylogenetic profiles (a vector with length of 50) for each gene. The vector value is the actual E-value obtained from the Basic Local Alignment Search Tool (BLAST) search.

c) Data Characterization

Separate individual operational relational databases are constructed to store the raw information from each of the above dimensions. There is no limit to the number of sources or dimensions which may be relied upon, although typically from five to twenty, preferably six to ten, are used. These databases provide the conventional query and search based on a single type of data source.

In additional to the raw data storage, each source is also converted into a numerical matrix. The result is what is called a characteristic matrix. Rows stand for genes of interest, and columns represent a particular attribute within that dimension. The element of the matrix is the value of each gene fit to that attribute.

The numerical matrix may be generated for each individual data source as follows.

For the functional assay, the row is the gene and the column is the assay type/name. The matrix element is the degree of inhibition or activation for each functional assay.

Specific protein-protein interactions are shown as a blue color assay in the YTH screening experiment. The binding affinity degree is is represented as one of four levels: strong, medium, weak, and none, corresponding to 1, 0.8, 0.6 and 0 in the binding matrix. The level of protein-protein interaction extracted from the proteomics experiment is based on eight internal experimental parameters. The row is the bait gene, the column is the hit gene. The element is the binding affinity described above.

For ontology mapping, a high-dimension word space is constructed by extracting the description words for each GO node and merging them with the key words parsed from the Medline title and abstract of each gene. Each unique key word is one dimension of the word space. The distances between each gene and the GO nodes are calculated and ranked by the Euclidean distance in the word space. The gene's definitive GO mapping nodes are either manually selected or the top five ranked GO nodes atre chosen to represent the relationship between the gene of interest and the GO vocabulary. The row of the matrix is the gene, the column is the unique description word from GO and the element is the mapping described above.

For fold recognition, the row of the matrix is the gene and the column is protein with crystal structure. The element is either zero if there is no match between the gene of interest to the crystal structure or the actual confidence score outputs from the neural network described in the previous section.

For the co-regulation value from the expression array, the row of the matrix is the gene and the column is the condition of the experiment performed. The element is the logarithm of the ratio of expression levels of a particular gene under two different experimental conditions.

For domain analysis, the row of the matrix is the gene and the column is the domain name obtained from Pfam. The element is the negative logarithm of the E-value obtained from the HMM search.

For protein links based on multiple genomes, the row of the matrix is the gene and the column is the name of the complete genome. The element is the actual negative logarithm of the lowest E-value obtained from the BLAST search queried by the gene against that particular complete genome.

Each characteristic matrix may be processed individually or by concatenating them into a larger matrix with multiple metric measurements as a part of the multidimensional analysis. Optionally, each matrix may be weighted using a variety of techniques. In one embodiment, each data source is equally weighted, i.e., with equal weight of 1. In another embodiment, based on prior knowledge, decrease the weight on data sources with higher false positives or less biological significance and/or increase the weight on more reliable or significant data. In a third embodiment, Bayesian statistics may be used to calculate the conditional posterior probability of the weight for each source based on the likelihood of observing the data based on the data source as the following:

$$P(S|D) = \frac{P(D|S) * P(S)}{\sum_{s} P(D|S) * P(S)}$$

where S is the data source, D is the characteristic value of each gene for that particular data source. P(D|S) is the likelihood of observing the data given this particular data source, P(S) is the a prior of the data source, which can be uniformly distributed in the beginning.

d) Data Integration

The data warehouse-based infrastructure supports bioinformatic analysis of potential molecular therapeutic targets. Unlike traditional relational database management systems (RDBMSs), which are optimized for transactional database processing, the data warehouse of this invention is an integrated, time-variant, nonvolatile collection of data from various operational databases. In this bioinformatics system, operational relational databases contain data generated from specific methodologies, as discussed above.

A gene-centric analysis of the data warehouse allows large-scale data integration, relationship learning, and decision-making based on daily updated operational relational databases. The entire system serves two primary purposes:

It organizes existing data to facilitate complex queries.

It infers relationships based on the stored data and subsequently predicts missing attribute values for incoming information based on multidimensional data.

Original data from a plurality of dimensions, or independent sources, is entered (i.e., parsed) into operational databases and updated daily. The operational databases are based on the relational database system and are tuned to support large-scale and frequent transactions. Data analysis engines extract, clean, and analyze the data from these databases and load the analyzed data and metadata into the data warehouse. The core data warehouse system design is based on the star schema of Oracle's 8i, which implements multidimensional databases.

Data marts (extensions of the data warehouse) support different query requests. Data marts derive data from the central data warehouse in response to different inquiries (i.e., queries). A detailed-summary system is a data mart built on the traditional RDBMS design with fixed metadata tables to summarize and aggregate raw data. Another type of data mart is based on a multidimensional database design. The latter offers superior representations of diverse data views, which it obtains by comparing various aspects of the analysis environment at different detail levels.

The star schema uses de-normalized storage to provide data views from individual or multiple dimensions with high efficiency. It offers multidimensional solutions that analyze large amounts of data with very fast response times, "slices and dices" through the data, and drills down or rolls up through various dimensions defined by the data structure. It is also easy to scale.

Figure 1:
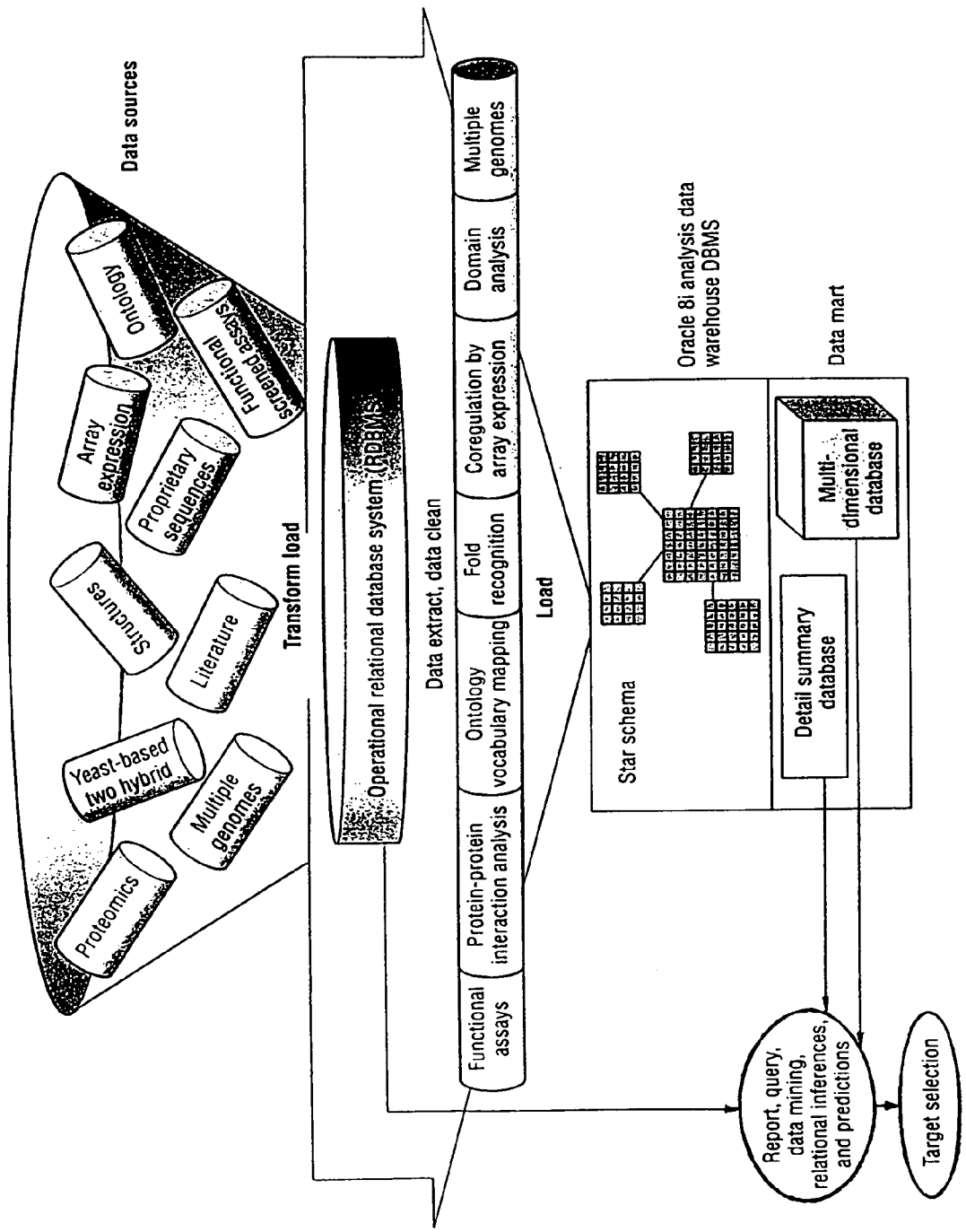
FIG. 1. Data analysis and data warehouse system. Data from various sources is input into the operational relational database system (RDBMS), extracted and cleaned, then loaded into the data warehouse system, which organizes the data and infers relationships among the stored data, predicting missing attribute values for incoming data.
Figure 2:
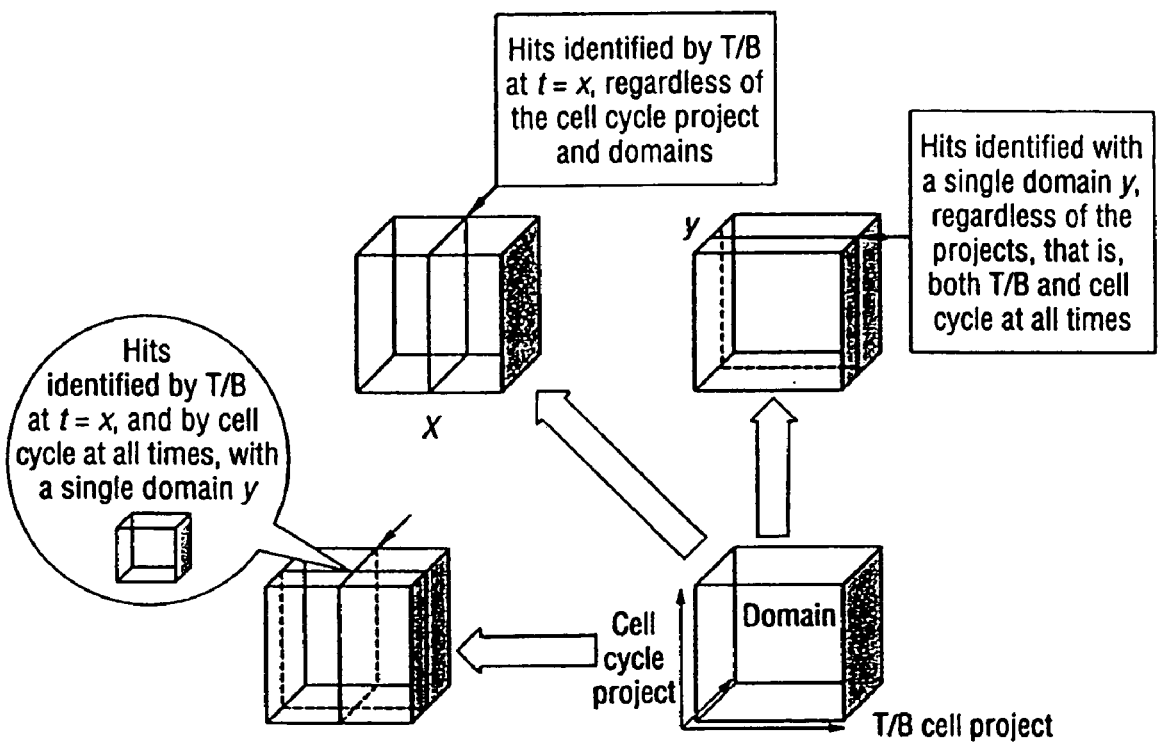
FIG. 2. Sample data view in a multidimensional database.

In order to easily visualize data from multiple views, the system is limited to a 3D data cube. In one example, genes discovered in the functional assays of two projects, a T and B lymphocyte cell project and cell-cycle project, are used to construct a data cube as a function of time and each gene's domains. As FIG. 2 shows, a cube slice represents a data view as a function of the various dimensions. Regular normalized RDBMS design requires expensive multiple table join operations to extract the information in the data cube, whereas the multidimensional database exploits the schema design to facilitate a faster and more reliable response.

d) Data Analysis and Relationship Inference

There are numerous methods known in the art to explore relationship extraction and inference deduction. In one embodiment, the system of this invention uses cluster analysis, a multivariate analysis technique that seeks to organize information about variables to form relatively homogeneous groups. Some common cluster analysis methods are hierarchical, k-mean, self-organizing, mapping, and support vector machines. All of these methods employ distance functions to compare raw data and recognize grouping characteristics.

Hierarchical clustering may be applied to the characteristic matrices. Hierarchical clustering offers flexibility in determining the exact cluster number and statistical assessment of members' relatedness along the branching tree (M. B. Eisen et al., Cluster Analysis and Display of Genome-Wide Expression Patterns, *Proc. Nat'l Academy of Science*, U.S.A. 95, Nat'l Academy of Sciences, Washington D.C., 1998, pp. 14,863-14,868). The distance matrix is based on the Pearson correlation coefficient between any of the two genes X and Y from the original characteristic matrix:

$$\rho_{x,y} = \frac{1}{N}\sum_{i=1}^{N}\left(\frac{X_i - \overline{X}}{\sigma_X}\right)\left(\frac{Y_i - \overline{Y}}{\sigma_Y}\right) \quad (1)$$

where N is the characteristic matrix dimension in the attribute direction, and σ is the standard deviation of the gene attribute.

$$\sigma_A = \sqrt{\sum_{i=1}^{N}\frac{(A_i - \overline{A})^2}{N}} \quad (2)$$

Clustering is achieved by recursively joining the two elements with the highest Pearson correlation coefficients in the upper-diagonal distance matrix until the distance matrix dimension reduces to one in the direction that the joining is performed. This process leads to clustering of genes with a similar binding vector profile. A tree-based dendrogram is produced with end nodes of relatively high correlation to each other, and nodes in the upper branch with less correlation to each other. The clustering algorithm uses an unsupervised hierarchical clustering that discovers common characteristics among genes without prior knowledge of them. As knowledge accumulates, it may be helpful to use a set of truly related genes as the training set for a relationship inference model.

Support vector machines (SVM), a class of supervised clustering algorithms, have been successfully applied to functional classification when combining data from both array expression experiments and phylogenetic profiles (P. Pavlidis et al., Gene Functional Classification from Heterogeneous Data, *Proc. 5$^{th}$ Int'l Conf. Computational Molecular Biology*, ACM Press, New York, 2001, pp. 242-248). SVM, projects the original data into a higher dimensional space, the feature space, and defines a separating hyperplane to discriminate class members from nonmembers, an operation difficult to perform in the original space. SVM does not require all clusters to have spherical contours, an underlying assumption of many unsupervised clustering algorithms, such as k-mean.

For supervised leaning, support vector machine with an inner product raised to a certain power (n=1, 2, 3) may be used $$K(\vec{X},\vec{Y})=((\vec{X}*\vec{Y}/\sqrt{\vec{X}*\vec{X}}\sqrt{\vec{Y}*\vec{Y}})+1)^n$$

or a radial basis kernel and a 2-norm soft margin $$K(\vec{X}*\vec{Y})=\exp(-\|\vec{X}-\vec{Y}\|^2/2\sigma^2)$$

where $\vec{X}$ is the vector from the matrix that describes gene X.

For supervised learning, feature selection is performed to extract the genes with the highest F score defined by the Fisher criterion to make the classification more accurate and informative:

$$F(j)=(\mu^+_j-\mu^-_j)^2/((\sigma^+_j)^2+(\sigma^+_j)^2)$$

Where $\mu^+_j$ and $\sigma^+_j$ are the mean and standard deviation of that feature across the positive examples, and $\mu^-_j$, $\sigma^-_j$ are from the negative examples.

Figure 5:
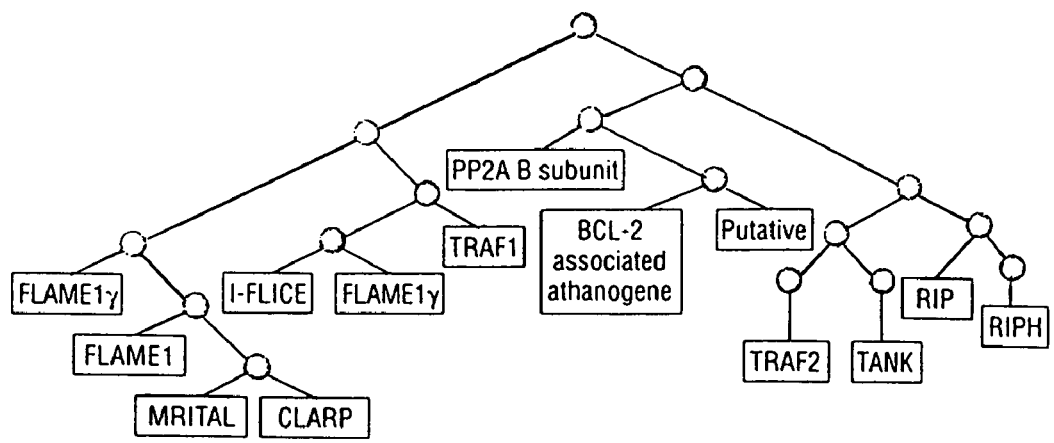
FIG. 5. Genes identified in the apoptosis pathway of the network are represented as a hierarchical tree format. The genes closer to each other on a branch of the tree have a higher correlation based on specific interactions in the YTH system.
Figure 6:
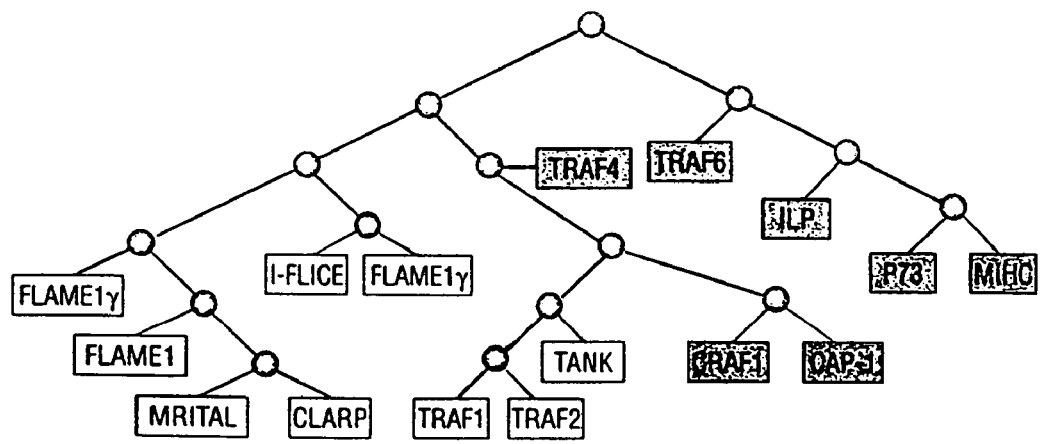
FIG. 6. Genes identified from the clustering analysis based on YTH and domain data. Genes in green are identified by YTH data, genes in blue are newly identified when domain data is added.

After clustering or other classification, genes with similar vector descriptions within the matrix may be correlated as demonstrated in FIGS. 5 and 6. Genes and proteins with similar profiles based on various biological experiment/observations described above are more likely to have similar cellular functions and be involved in the same biological pathway.

Genes and proteins having similar functions or participating in the same biological pathway are clustered/classified together. Therefore, functions of novel genes and proteins can be inferred based on functions of the known genes or proteins in the same cluster.

The system effectively blends all available information to establish functional linkages among proteins. This information may be used to identify genes that are likely drug target candidates. Small molecule-based high throughput screening (HTS) of the validated targets may be used to identify lead compounds. The lead compounds may then be subjected to downstream biochemical and cell-based assays for optimization. After confirming the functional specificity and activity of the optimized lead compounds, their drug effects may be further characterized in animal models and preclinical studies.

EXAMPLE

Figure 3:
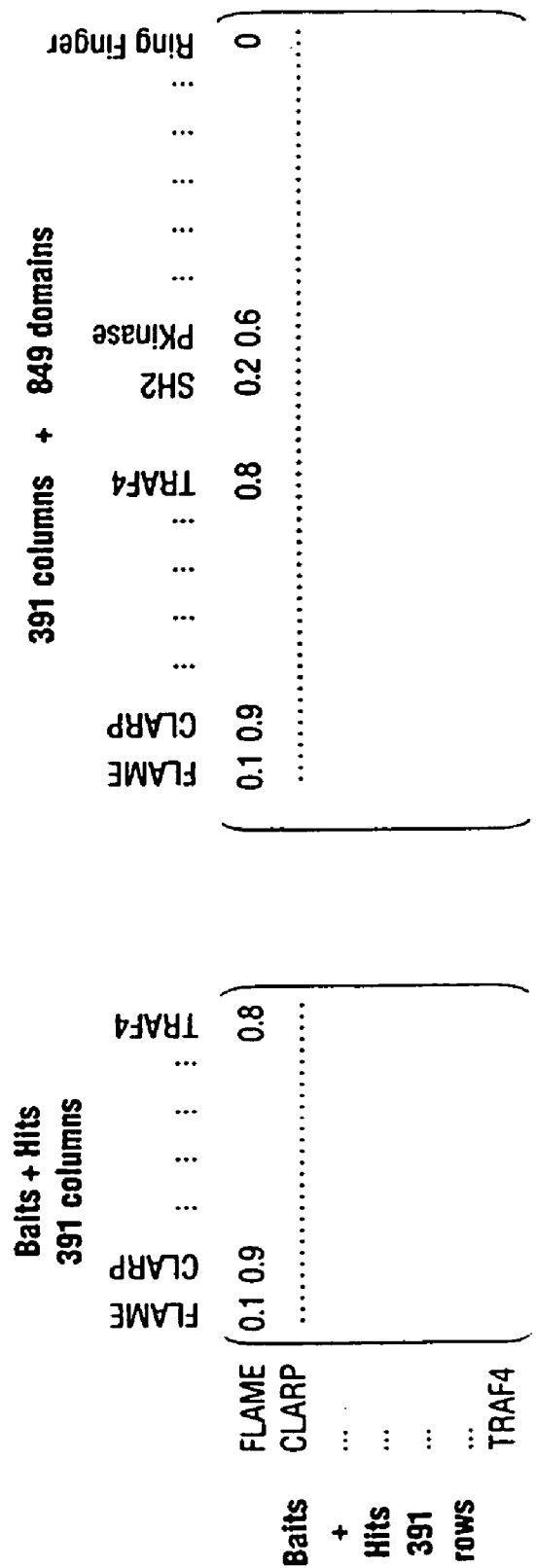
FIG. 3. Analysis of two characteristic matrices. The left panel matrix has the same cardinality in both dimensions. The matrix contains each gene's binding patterns. Domain analysis of each of the 391 genes resulted in a total of 849 domains as shown in the right panel. The negative normalized logarithm of the F-value was concatenated to the first matrix as shown in the right panel.
Figure 4:
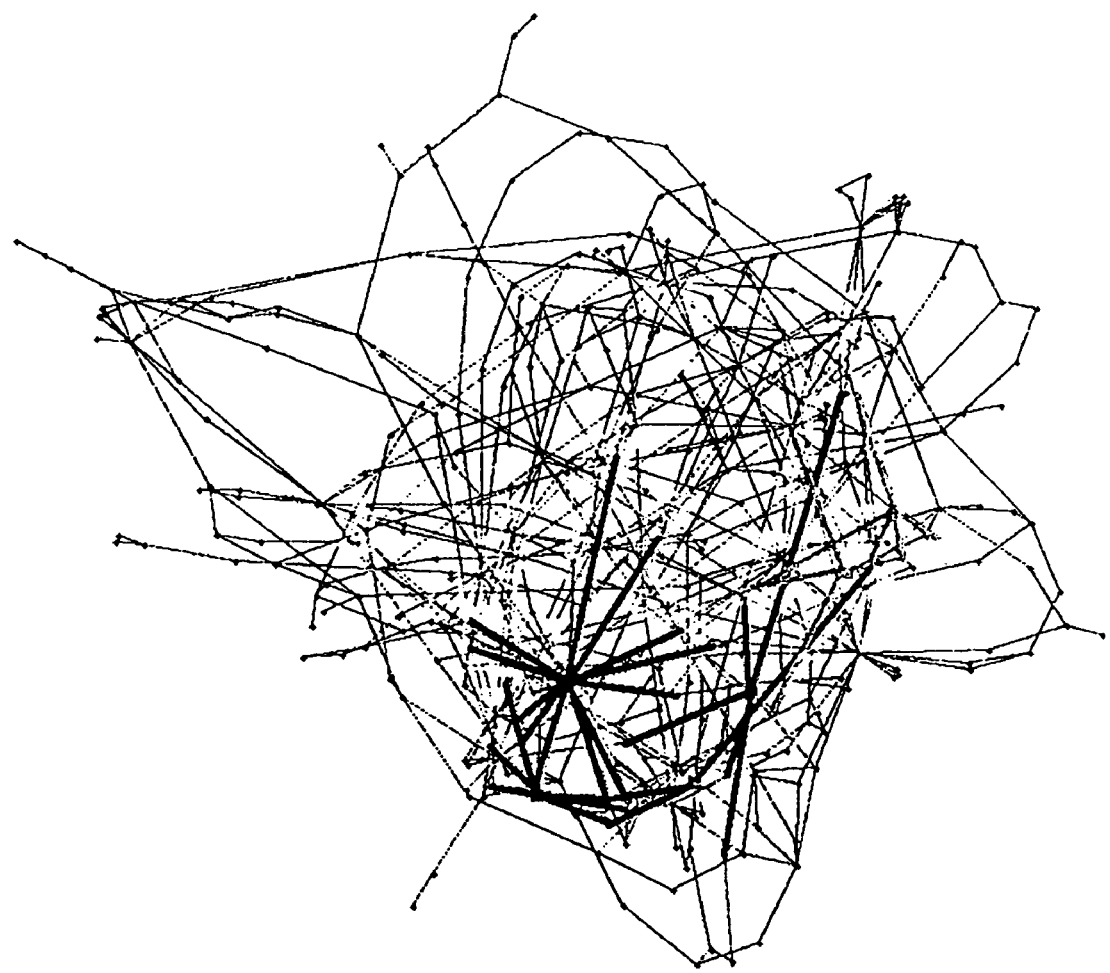
FIG. 4. A protein-protein interaction network in a human cell probed by the YTH system. Each gene is represented by a gray dot, and the edges connecting two genes represent specific interactions between the genes. For the apoptosis example, green represents the genes from the YTH matrix analysis, and blue represents additional genes from analyses of both YTH and domain information. As the network demonstrates, TNF-induced apoptosis pathway members (blue and green) are scattered in the YTH network, whereas domain information links them together.

Clustering methods were used to analyze genes from YTH screening. The original data set contained about 300 baits and 2,300 hits. A total of 391 baits and hits with multiple interactions were selected for the analysis shown in FIG. 3. FIG. 4 shows the protein-protein interaction network prior to gene clustering.

After clustering the first characteristic matrix, proteins that have similar functions or participate in the same pathway were grouped. As shown in FIG. 5, FLAME1-γ (AF009618), *Homo sapiens* FLAME1 mRNA (Af009616), MRIT-α-1 (U85059), I-FLICE (AF041458), and CLARP (AF005774.1) all encode the same protein, which is commonly referred to as FLIP. FLIP is a death-domain-containing anti-apoptotic molecule that regulates Fas/NFR1-induced apoptosis.

Another group close to FLIP in the hierarchical tree contains TRAF1 (TNF receptor associated factor 1, NM_005658), TRAF2 (U12597), TANK (TRAF family member associated NFKB activator, XP_002533.1), receptor interacting protein (RIP), RIP-like kinase (AF156884), BCL-2 associated atlianogene (XP_005538.1), protein phosphatase 2 regulatory subunit B (NP_006234.1), and an unknown gene (BAB25712.1).

The literature has shown that TNF receptors lack intrinsic catalytic activity. Death-domain-containing proteins RIP and TRAF-domain-containing proteins TRAF1, TRAF2, TRAF3) bridge TNF receptors to several downstream signaling pathways. This bridging causes diverse cellular responses including cellular proliferation, differentiation, effector functioning, and apoptosis. Protein phosphatase 2A (PP2A) affects a variety of biological events including apoptosis.

BAD is a pro-apoptotic member of the BCL2 family of proteins. PP2A can dephosphorylate BAD, resulting in apoptosis. BCL-2-associated athanogene (BAG-1) is a heat shock 70-(Hsp70)-binding protein that can collaborate with BCL-2 to enhance the anti-apoptotic activity of BCL-2.

The literature confirms that these proteins are all involved in apoptotic and anti-apoptotic signaling events initiated by TNF and BCL-2. The unknown protein BAB25712.1 might therefore play a role in TNF or BCL-2 signaling pathways. Our system placed FLIP in the vicinity of RIP and the BCL-2-associated chaperon BAG-1. Several independent studies support this protein linkage assignment. FLIP can modulate the NFkappaB pathway and physically interacts with several signaling proteins, such as the TRAFS and RIP. FLIP can also interact with a BCL-2 family member.

FIG. 6 shows the significant refinement in results when HMM domain search information was incorporated as an additional dimension. First, more proteins involved in TNF receptor-induced apoptosis join the group. Both CAP-1 (CD40-associated protein, L38509) and CRAF-1 (CD40 receptor-associated factor 1, U21092) sequences are essentially identical to TRAF3 by BLAST analysis (in other words, TRAF3 is included in this pathway).

TRAF3, which contains a conserved TRAF domain, binds to the CD40 (a member of the TNF receptor family) intracellular domain. Two other TRAF family members, TRAF4 and TRAF6, were included in this group. ILP (IAP-like protein, U32974), MIHC (human homolog of IAP C, U37546), and p73 (AF079094) were also found to be new members.

Baculovirus inhibitors of apoptosis (IAPs) can prevent insect cell death. Both ILP and MIHC are human homologs of LAP. Rothe and colleagues have shown that interactions of MIHC with TRAF1 and TRAF2 inhibit apoptosis. Similarly, ILP can regulate cell death. P73 is a p53-like tumor-suppressor protein which regulates the cell cycle and apoptosis. Direct interaction of p73 with LAP-like proteins or TRAFs has not been reported, however. The inference analysis suggests that the apoptosis pathways of p73 and IAP-like proteins intersect or even associate physically.

We excluded genes specific to the BCL-2 apoptosis pathway, PP2A B subunit, and BCL2-associated athanogen, as the current apoptotic pathway is more TNF specific. Finally, we also excluded two related proteins (RIP and RIPH) after we added domain information. We did this to weight the YTH interaction pattern and domain information equally. When we tuned the domain weight up to five times the weight of YTH, RIP, and RIPH were retained, and we also introduced some unrelated proteins.

Although specific embodiments of the invention have been described, various modifications, alterations, alternative constructions, and equivalents are also encompassed within the scope of the invention. The described invention is not restricted to operation within certain specific data processing environments, but is free to operate within a plurality of data processing environments. Additionally, although the present invention has been described using a particular series of transactions and steps, it should be apparent to those skilled in the art that the scope of the present invention is not limited to the described series of transactions and steps.

Further, while the present invention has been described using a particular combination of hardware and software, it should be recognized that other combinations of hardware and software are also within the scope of the present invention. The present invention may be implemented only in hardware, or only in software, or using combinations thereof.

The specification and drawings are, accordingly, to be regarded in an illustrative rather than a restrictive sense. It will however, be evident that additions, subtractions, deletions, and other modifications and changes may be made thereunto without departing from the broader spirit and scope of the invention as set forth in the claims.

We claim:

1. A method for identifying biomolecule functions and relationships via the manipulation of biological data from a plurality of sources, comprising:

collecting biological data from a plurality of sources, wherein a source contains different attributes of biological data than another source;

calculating for each source a characteristic matrix from the biological data for that source, wherein each characteristic matrix has a first dimension representing biomolecules and a second dimension representing attributes from the corresponding source, wherein each matrix element has a value for a specific biomolecule fit to a specific attribute;

combining the characteristic matrices to create a combined matrix of higher dimension than each of the characteristic matrices, wherein combining includes calculating a weighting coefficient corresponding to each of the characteristic matrices; and analyzing the combined matrix to determine at least one of biomolecule functions and relationships, wherein analyzing comprises clustering the biomolecules is based on global similarity criteria between the biomolecules, wherein a global similarity criterion between two biomolecules is composed from similarity criteria between the values of each attribute of each source for the two biomolecules.

2. The method of claim 1, wherein the at least one of biomolecule functions and relationships includes protein-protein interactions.

3. The method of claim 1, wherein clustering comprises performing an unsupervised clustering analysis.

4. The method of claim 1, wherein clustering the comprises using support vector machines or neural nets.

5. The method of claim 1, wherein a global similarity criterion is the distance from one biomolecule to another biomolecule in the higher dimensional space of the combined matrix.

6. The method of claim 1, wherein a global similarity criterion utilizes a Pearson correlation coefficient relating one biomolecule to another biomolecule in the higher dimensional space of the combined matrix.

7. The method of claim 1, wherein the sources comprise at least one source from a plurality of screening experiments and at least one source from a plurality of public or proprietary archival resources.

8. The method of claim 7, wherein the plurality of screening experiments comprise high throughput screening, yeast two-hybrid screening, protein array analyses, nucleic acid array analyses, SiRNA analyses, and functional gene screening.

9. The method of claim 7, wherein biological data from the plurality of public or proprietary archival resources comprise domain analyses, ontology vocabulary mapping, fold recognition, gene sequences, protein sequences, expressed sequence tags, single nucleotide polymorphisms, biochemical functions, physiological roles and structure/function relationships from web-based or conventional published literature.

10. The method of claim 1, wherein a weighting coefficient is determined using Bayesian statistics.

11. The method of claim 1, further comprising identifying potential therapeutic targets based on the analysis.

12. The method of claim 1 wherein combining includes: for each characteristic matrix, multiplying the matrix elements of that characteristic matrix by the weighting coefficient for that characteristic matrix, wherein the weighting coefficients for two of the characteristics matrices are different.

13. A computer readable storage medium having a plurality of instructions to direct a processing device to perform an operation for identifying biomolecule functions and relationships via the manipulation of biological data from a plurality of sources, the operation comprising the steps of:
collecting biological data from a plurality of sources;
calculating for each source a characteristic matrix from the biological data for that source, wherein each characteristic matrix has a first dimension representing biomolecules and has a second dimension representing attributes from the corresponding source, wherein each matrix element has a value for a specific biomolecule fit to a specific attribute;
combining the characteristic matrices to create a combined matrix of higher dimension than each of the characteristic matrices, wherein combining includes calculating a weighting coefficient corresponding to each of the characteristic matrices; and
analyzing the combined matrix to determine at least one of biomolecule functions and relationships, wherein the analyzing comprises clustering the biomolecules based on global similarity criteria between the biomolecules, wherein a global similarity criterion between two biomolecules is composed from similarity criteria between the values of each attribute of each source for the two biomolecules.

14. The computer readable storage medium of claim 13 wherein combining includes:
for each characteristic matrix, multiplying the matrix elements of that characteristic matrix by the weighting coefficient for that characteristic matrix, wherein the weighting coefficients for two of the characteristics matrices are different.

15. A method for identifying biomolecule functions and relationships via the manipulation of biological data from a plurality of sources, comprising:
collecting biological data from a plurality of sources, wherein a source contains different attributes of biological data than another source, wherein the biological data from each source contains a list of biomolecules, a list of attributes from that source, and a value for each biomolecule for each attribute from that source;
and clustering the biomolecules according to the values for the attributes from the plurality of sources to determine at least one of biomolecule functions and relationships, wherein clustering the biomolecules is based on global similarity criteria between the biomolecules, wherein a global similarity criterion between two biomolecules is composed from similarity criteria between the values of each attribute of each source for the two biomolecules, wherein a global similarity criterion utilizes different weighting coefficients for values of the attributes of two of the sources.

16. The method of claim 15, wherein a global similarity criterion is a distance from one biomolecule to another biomolecule, wherein the distance is calculated from a difference between the values of each attribute of each source for the two biomolecules.

17. The method of claim 15, wherein a global similarity criterion utilizes a Pearson correlation coefficient relating, one biomolecule to another biomolecule by using the values of each attribute of each source for the two biomolecules.

18. The method of claim 15 wherein a lower weighting coefficient is used for the values of the attributes from a source with higher false positives than for the values of the attributes from a source with lower false positives.

* * * * *